United States Patent
Dahan et al.

(10) Patent No.: US 7,896,835 B2
(45) Date of Patent: *Mar. 1, 2011

(54) APPARATUS AND METHOD FOR MEASURING FLUID FLOW TO A SUCKLING BABY

(75) Inventors: Haim Emil Dahan, Raanana (IL); Jose Mario Meschiany, Tel Aviv (IL); Lipa Leon Roitman, Dayton, OH (US)

(73) Assignee: Kaizen International Technologies Biotech, Inc. LLP, Raanana (IL)

( * ) Notice: Subject to any disclaimer, the term of this patent is extended or adjusted under 35 U.S.C. 154(b) by 1846 days.

This patent is subject to a terminal disclaimer.

(21) Appl. No.: 10/774,939

(22) Filed: Feb. 9, 2004

(65) Prior Publication Data
US 2005/0177099 A1  Aug. 11, 2005

(51) Int. Cl.
*A61J 7/00* (2006.01)
(52) U.S. Cl. .................................... 604/76; 604/73
(58) Field of Classification Search ............ 604/73, 604/74, 75, 76, 77; 239/33; D7/300.2; 215/11.1, 215/DIG. 3; 73/1.36, 1.73, 1.74
See application file for complete search history.

(56) References Cited

U.S. PATENT DOCUMENTS

| 322,508 | A | | 7/1885 | Ware |
| 1,032,518 | A | | 7/1912 | Thieringer |
| 3,260,462 | A | * | 7/1966 | Smaczny ............... 239/33 |
| 3,790,016 | A | * | 2/1974 | Kron ................. 215/11.1 |
| 3,895,533 | A | | 7/1975 | Steier |
| 4,232,687 | A | | 11/1980 | Anderson-Shanklin |
| 4,687,466 | A | * | 8/1987 | Larsson ................. 604/82 |
| 5,078,734 | A | | 1/1992 | Noble |
| 5,222,940 | A | * | 6/1993 | Wilk ..................... 604/77 |
| 5,263,599 | A | * | 11/1993 | Sklar .................. 215/11.1 |
| D391,642 | S | | 3/1998 | Fountain |

(Continued)

FOREIGN PATENT DOCUMENTS

EP  1 430 918 A  6/2004

(Continued)

OTHER PUBLICATIONS

Woolridge, M.W. "The continuous measurement of milk intake at a feed in breast-fed babies". Sep. 1982. Early Human Development. vol. 6. pp. 365-373.*

(Continued)

*Primary Examiner*—Kevin C Sirmons
*Assistant Examiner*—Laura C Schell
(74) *Attorney, Agent, or Firm*—Finnegan, Henderson, Farabow, Garrett & Dunner L.L.P (57) ABSTRACT

A system for measuring fluid intake by a sucking baby. The system includes: a feeding pathway for fluid flow from the fluid source to the baby's mouth, wherein the feeding pathway has a first opening in communication with the fluid source and a second opening in communication with the baby's mouth; and an indicator pathway for indicating the amount of fluid provided to the baby's mouth through the feeding pathway, wherein the indicator pathway has a first opening in communication with the fluid source and a second opening in communication with the baby's mouth. The amount of fluid drawn into the indicator pathway is indicative of the amount of fluid drawn into the feeding pathway.

30 Claims, 12 Drawing Sheets

U.S. PATENT DOCUMENTS

| | | | | |
|---|---|---|---|---|
| 5,827,191 | A | * | 10/1998 | Rosenfeld .................. 600/476 |
| 6,033,367 | A | | 3/2000 | Goldfield |
| 6,109,100 | A | * | 8/2000 | Buckley et al. ............... 73/198 |
| 6,113,625 | A | | 9/2000 | Foley |
| 6,588,613 | B1 | * | 7/2003 | Pechenik et al. ........... 215/11.1 |
| 6,741,523 | B1 | * | 5/2004 | Bommarito et al. ......... 368/327 |
| 2004/0055987 | A1 | * | 3/2004 | Paige ........................ 215/11.1 |
| 2008/0039741 | A1 | * | 2/2008 | Shemesh et al. ............ 600/584 |

FOREIGN PATENT DOCUMENTS

| | | | |
|---|---|---|---|
| WO | WO 01/54488 A1 | | 8/2001 |
| WO | WO 2005/016220 | * | 2/2005 |

OTHER PUBLICATIONS

Office Action dated Nov. 28, 2007, issued in co-pending U.S. Appl. No. 11/300,515.

Office Action dated Sep. 15, 2008, issued in co-pending U.S. Appl. No. 11/300,515.

Office Action dated Jan. 9, 2009, issued in co-pending U.S. Appl. No. 11/300,515.

Office Action dated Aug. 3, 2009, issued in co-pending U.S. Appl. No. 11/300,515.

Office Action dated Feb. 18, 2010, issued in co-pending U.S. Appl. No. 11/300,515.

International Search Report , Mailing Dated May 25, 2005; and Written Opinion of the International Searching Authority.

International Search Report , Date of Mailing Jun. 5, 2007; Notification of Transmittal of The International Search Report and the Written Opinion of The International Searching Authority or the Declaration.

* cited by examiner

Prior Art

APPARATUS AND METHOD FOR MEASURING FLUID FLOW TO A SUCKLING BABY

TECHNICAL FIELD

This invention relates generally to methods and systems for indicating fluid flow, and more specifically to methods and systems for indicating fluid flow by utilizing the suction induced by a suckling infant on more than one pathway.

BACKGROUND

The number one question of new parents is: "Is my baby getting enough to eat?" Usually, a newborn baby will eat at least 8 to 12 times in 24 hours during the first 4 to 6 weeks of life. Most babies need at least one nighttime feeding during the first 6 to 8 weeks of life. In the absence of any way to measure the amount of milk or formula the baby receives, the mother has to follow the subjective signs that her baby gives to her. This problem is particularly present in the case of mothers who breast-feed their babies.

In order to measure the volume of fluid supplied to a baby, those skilled in the art have utilized complex, electronic flow measurement systems. Such systems typically involve attaching electronic or electromechanical flow meters to a fluid flow passage in order to measure the fluid flow. However, such systems are expensive and complex, requiring the attachment of bulky systems to the milk or formula supply. In addition, the use of such systems is limited to bottle feeding systems and is not applicable to breast-feeding infants. As the benefits of breast-feeding have become widely known, more mothers are breast-feeding than in the past, highlighting the need for a method to indicate a baby's fluid intake.

Apparatus and methods consistent with the present invention are directed at overcoming one or more of the problems associated with the prior art systems.

SUMMARY

A method consistent with the principles of the present invention includes: providing a feeding pathway for fluid flow from the fluid source to the baby's mouth, wherein the feeding pathway has a first opening in communication with the fluid source and a second opening in communication with the baby's mouth; and providing an indicator pathway for indicating the amount of fluid provided to the baby's mouth through the feeding pathway, wherein the indicator pathway has a first opening in communication with the fluid source and a second opening in communication with the baby's mouth. The amount of fluid drawn into the indicator pathway is indicative of the amount of fluid drawn into the feeding pathway.

An apparatus consistent with the principles of the present invention includes: a feeding pathway for fluid flow from the fluid source to the baby's mouth, wherein the feeding pathway has a first opening in communication with the fluid source and a second opening in communication with the baby's mouth; and an indicator pathway for indicating the amount of fluid provided to the baby's mouth through the feeding pathway, wherein the indicator pathway has a first opening in communication with the fluid source and a second opening in communication with the baby's mouth. The amount of fluid drawn into the indicator pathway is indicative of the amount of fluid drawn into the feeding pathway.

A method consistent with the principles of the present invention includes: receiving suction from a baby's mouth; providing the suction to at least a first pathway and a second pathway; and indicating in the second pathway the presence of the suction.

The foregoing background and summary are not intended to be comprehensive, but instead serve to help artisans of ordinary skill understand the following implementations consistent with the invention set forth in the appended claims. In addition, the foregoing background and summary are not intended to provide any independent limitations on the claimed invention.

BRIEF DESCRIPTION OF THE DRAWINGS

The accompanying drawings show features of implementations consistent with the present invention and, together with the corresponding written description, help explain principles associated with the invention. In the drawings.

DETAILED DESCRIPTION

The following description refers to the accompanying drawings in which, in the absence of a contrary representation, the same numbers in different drawings represent similar elements. The implementations in the following description do not represent all implementations consistent with the claimed invention. Instead, they are merely some examples of systems and methods consistent with the invention.

Embodiments of the present invention utilize a "milk split principle" to exploit a baby's suction to distribute a fluid source, for example, milk from a mother's breast, milk from a bottle, or formula from a bottle, into two or more pathways. In the case of a two pathway system, having an indicator pathway and a feeding pathway, the amount of fluid that goes into the indicator pathway is indicative of the amount of fluid that goes into the feeding pathway.

The milk split principle described above is caused by the baby's sucking and may be used, among other things, to give an indication of the total milk the baby took in, the sucking pressure of the baby, or merely an indication that the baby has some intake. While the milk split principle utilizes the baby's suction to measure fluid flow, the baby does not have to work any harder than normal in the course of feeding. The amount of fluid drawn into and retained in the indicator pathway is indicative of the amount of fluid drawn into the feeding pathway. The apparatus may be configured such that the amount of fluid provided to the baby's mouth through the feeding pathway is proportional to the amount of fluid drawn into and retained in the indicator pathway.

A feeding measuring device ("FMD") consistent with the principles of the present invention includes a feeding pathway and an indicator pathway. The feeding pathway has a first opening in communication with the milk source and a second opening in communication with the baby's mouth via the feeding pathway by providing, for example, one or more gradations along the indicator pathway with the gradations having markings indicating fluid volumes. The indicator pathway has a first opening in communication with the milk source and a second opening in communication with the baby's mouth. Because the negative pressure drawn by the baby's mouth upon both the indicator pathway and the feeding pathway is the same, the amount of milk drawn into the indicator pathway is indicative of the amount of milk drawn into the feeding pathway.

The openings of the feeding pathway and the indicator pathway in communication with the baby's mouth may be formed by Y-branches of a milk delivery pathway. This assists in providing proportional pressure from the baby's sucking to both the feeding pathway and the indicator pathway.

In order to facilitate greater resolution of the volume of fluid taken in by the baby through the feeding pathway, the indicator pathway may be of smaller cross-sectional area, of longer length than the feeding pathway, or a combination of both.

An FMD may be separate from or an integral part of a nipple. An FMD integrated with a nipple, or integrated FMD ("IFMD"), may be affixed to the mother's breast during breastfeeding or may be manufactured to be affixed to a bottle. When affixed to the mother's breast, the IFMD indicates via the indicator pathway the amount of milk that flows out of the mother's nipple through the feeding pathway to the baby's mouth. By breastfeeding the baby through an IFMD, the mother not only receives an indication of the milk flow to her baby, but may also relieve the mother of sore or cracked nipples sometimes associated with breastfeeding.

During breastfeeding through the IFMD, the baby latches onto the nipple tip of the IFMD and begins to feed. The negative pressure induced into the feeding pathway and indicator pathway draws the mother's milk into both pathways. The milk flows through the relatively large feeding pathway into the baby's mouth, while also being slowly drawn into the relatively smaller indicator pathway. Because negative pressure from the suckling infant is applied to both the feeding pathway and the indicator pathway, the amount of milk flowing into the indicator pathway is indicative of the amount of milk that goes through the feeding pathway. In this manner, one can easily see on the indicator pathway the total volume of fluid consumed by the baby through the feeding pathway. In practice, the indicator pathway may be designed of such length and cross-section, so that it may contain a sufficient volume of milk to indicate the intake for a single feeding without "spilling over" into the baby's mouth. Therefore, greater volume indicator pathways (e.g., longer length, greater cross-sectional area, multiple indicator pathways, or a combination of the aforementioned) may be used with larger babies, and correspondingly, smaller volume indicator pathways may be used with smaller infants. A wide variety of designs may be manufactured to suit the baby's size, weight, and age, as well as for variations in a mother's breast or nipple size.

Figure 1:
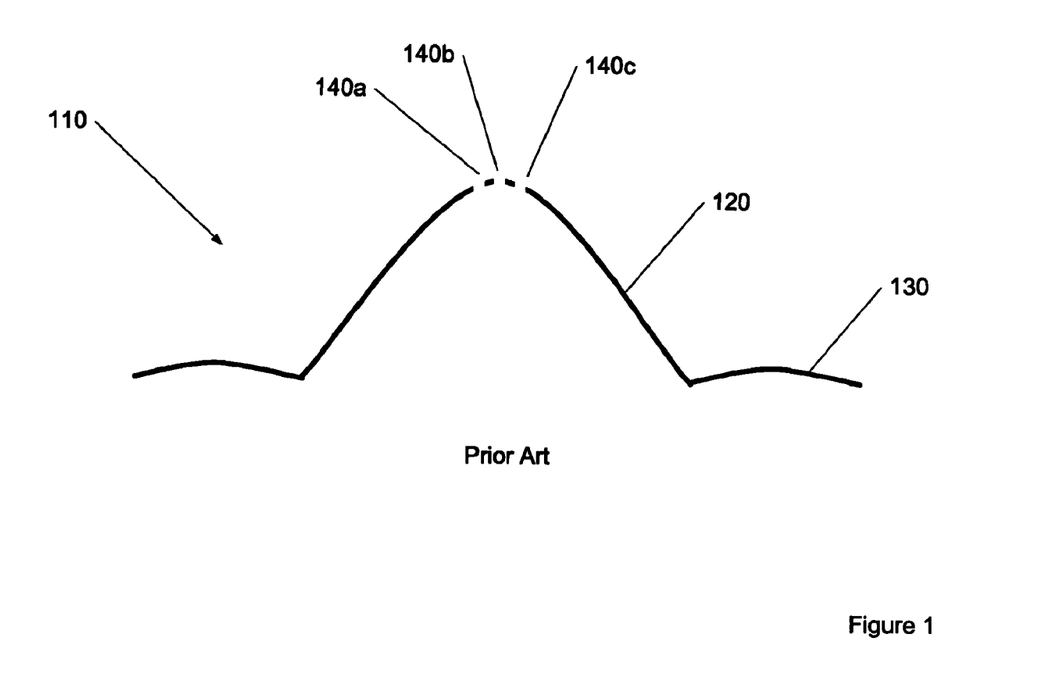
FIG. 1 illustrates a side cross-section view of a prior art nipple protector.

FIG. 1 illustrates a side cross-section view of a prior art nipple protector 110. The nipple protector 110 comprises a nipple tip 120 that arises out of a nipple base 130. The nipple tip 120 includes one or more nipple apertures 140. Nipple protector 110 is affixed to the mother's breast, such that when a baby sucks on the nipple tip 120 milk flows out of the mother's nipple and through the apertures 140 in nipple tip 120 into the baby's mouth.

Figure 2:
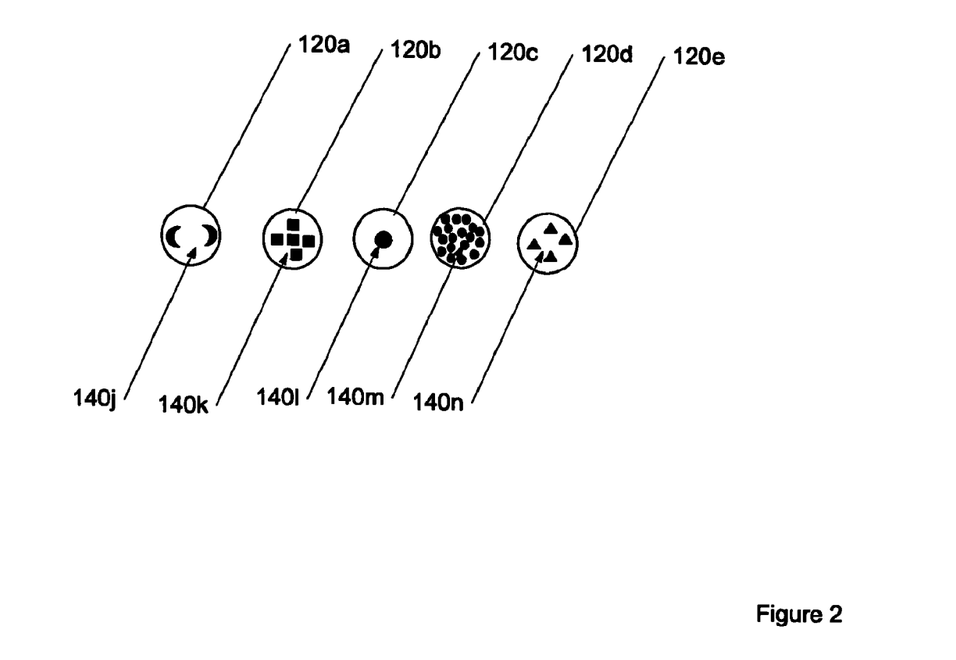
FIG. 2 illustrates a variety of top-down views of possible arrangement, sizes, and shapes of apertures possible in a nipple or nipple protector.

Those skilled in the art will appreciate that nipple protectors are not limited to the shape or features mentioned in the previous paragraph. For example, the nipple tip 120 may feature a plurality of apertures in different geometric arrangements and sizes. FIG. 2 illustrates a variety of top-down views of possible arrangement, sizes, and shapes of apertures possible in a nipple or nipple protector 110. For example, nipple tips 120a-e are illustrated with a variety of apertures 140j-n. The IFMD may also comprise similar aperture geometries.

Figure 3:
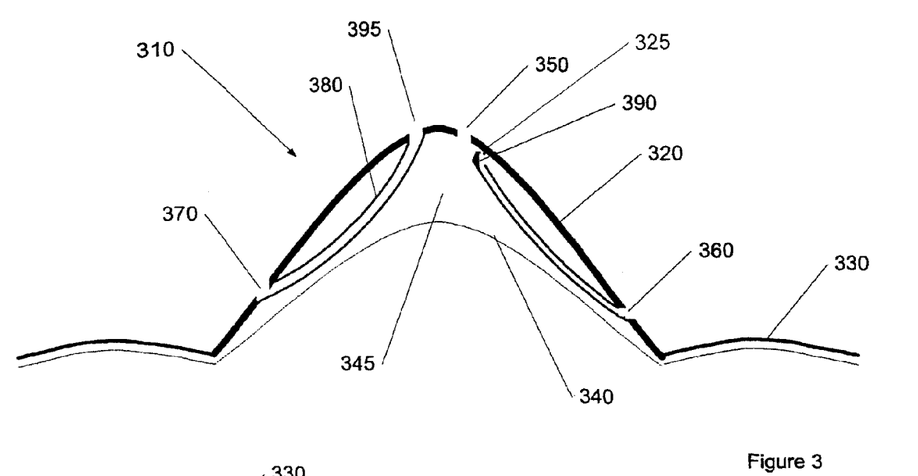
FIG. 3 illustrates a cross-sectional side view of an integrated feeding measuring device ("IFMD") consistent with the present invention.
Figure 3A:
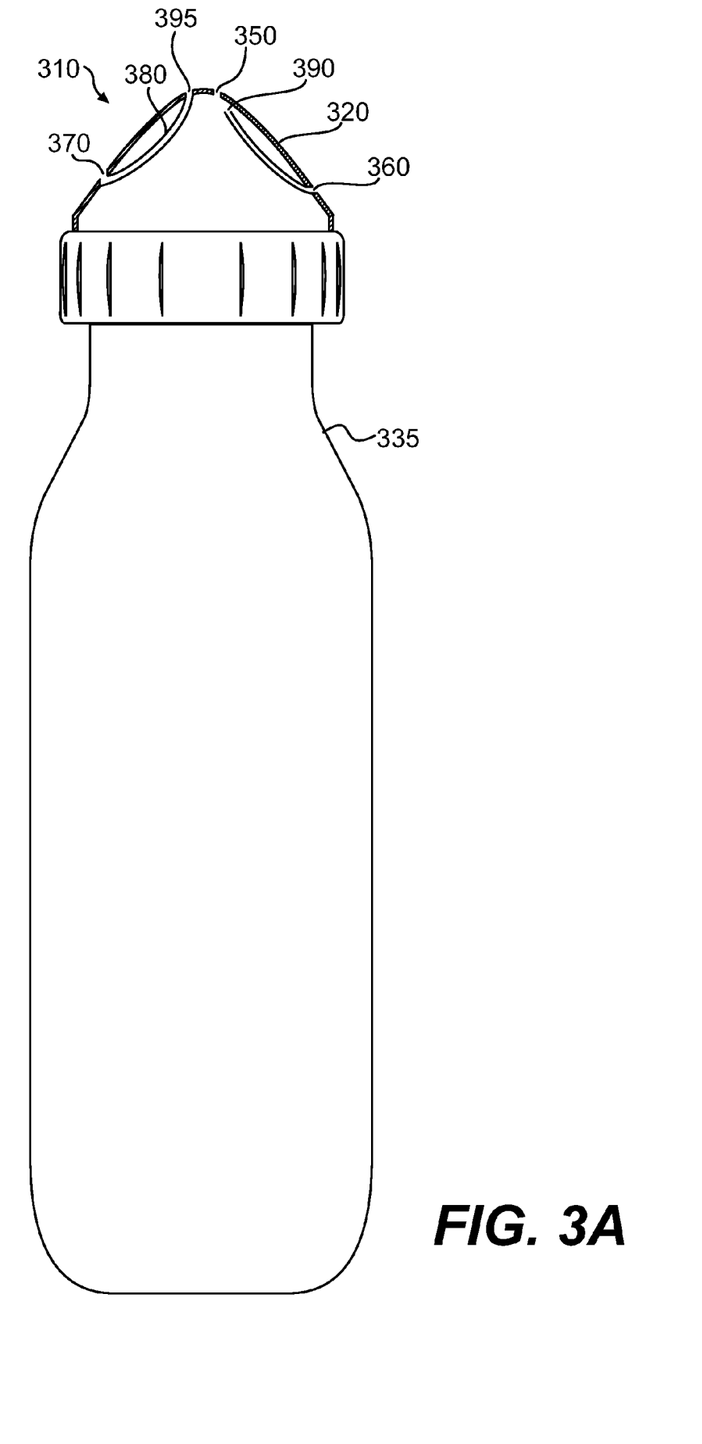

FIG. 3 illustrates a cross-sectional side view of an IFMD consistent with the present invention. The IFMD 310 is affixed to a woman's breast 340. The nipple tip 320 merges into a nipple base 330. When placed upon the breast 340, a milk cavity area 345 is formed between the nipple tip 320 and the breast 340. When a baby sucks on the nipple tip 320, negative pressure is transmitted through the feeding pathway 350 that communicates the pressure from the baby's mouth to the breast 340. This draws milk into the milk cavity area 345 and into the baby's mouth through the feeding pathway 350. While a single feeding pathway 350 is illustrated in FIG. 3, those skilled in the art will appreciate that multiple feeding pathways 350 of various shapes, sizes, and arrangements could be used. FIG. 3A illustrates an embodiment of the present invention wherein the fluid source is a bottle 335.

As the baby applies negative pressure through feeding pathway 350, the same negative pressure is applied to indicator pathway 380 at first aperture 395. Indicator pathway 380 has a second aperture 390 in communication with the milk cavity area 345, so that the pressure is transmitted through the indicator pathway 380 to draw milk from the milk cavity area 345 into the indicator pathway 380 through second aperture 390. To assist in consistent operation of the present invention, the second aperture 390 of the indicator pathway 380 may be placed such that it is normally always in communication with milk in the milk cavity area 345. Indicator pathway 380 is more easily seen and understood with respect to FIG. 4.

Figure 4:
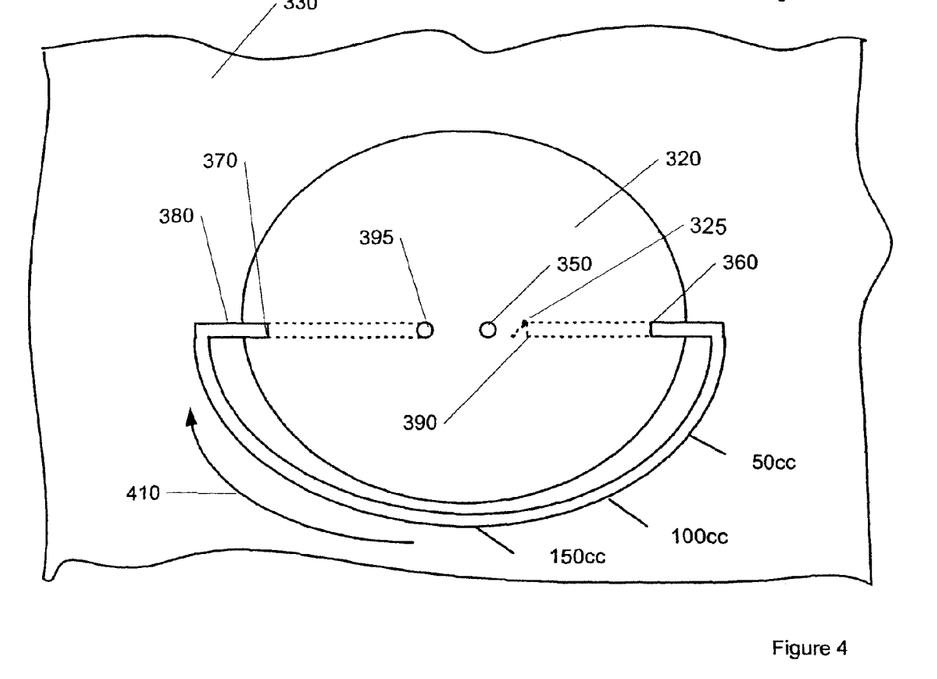
FIG. 4 illustrates a top-down view of an IFMD consistent with the present invention.

FIG. 4 illustrates a top-down view of the IFMD of FIG. 3 consistent with the present invention. In the illustrated IFMD, the indicator pathway second aperture 390 opens into the milk cavity area 345. The indicator pathway 380 then exits to the nipple base 330 through a first nipple tip transition aperture 360, wraps around the nipple base, and returns through a second nipple tip transition aperture 370 to provide the first aperture 395 to receive the baby's sucking negative pressure. As the baby sucks, the indicator pathway intakes milk which travels in the direction indicated by arrow 410.

Gradations, for example, as illustrated by 50 cc, 100 cc, and 150 cc, may be placed at one or more points along the indicator pathway, so that the total volume of fluid received by the baby through the feeding pathway can be read. Later in this specification, the calculations to generate the gradation numbers are provided. Those skilled in the art will appreciate that gradations are not necessary to indicate fluid flow, but are merely useful in indicating approximate amounts of fluid taken by the baby. For example, it is consistent with the principles of the present invention to provide no gradations or to provide a single gradation to indicate when the baby has taken in a sufficient amount. Or, for example, a colored zone may be used to indicate an appropriate intake for the baby. Along these lines, FMD's or IFMD's may be manufactured in with various features on, in, or along the indicator pathway depending on the size, age, or weight of the baby.

Consistent with the principles of the present invention, any number of indicator pathways may be provided. The indicator pathways may be of any shape, length, diameter, and resistance. As understood by those skilled in the art, different materials may be used to construct the indicator pathway and the nipple. The indicator pathway may be constructed of a translucent material, so that the amount of fluid in the indicator pathway may be clearly seen. Or, the indicator pathway may be constructed of a material that changes color upon contact with the fluid. Those skilled in the art will appreciate that the FMD or IFMD may be constructed of a reusable or disposable material.

The indicator pathway, and other features of the present invention, may be constructed integrally with the nipple or as a separate attachment. It should be understood that the path of the indicator pathway and its exact placement is unimportant to the present invention. So long as the pressure from the baby's sucking is applied to one end of the indicator pathway and the fluid source is placed at the other end of the indicator pathway, the invention will function properly. The indicator pathway may be placed within the nipple tip and base, on the nipple tip and base, in the nipple tip and base, or any combination of the above. In addition, multiple indicator pathways and feeding pathways may be used.

The indicator pathway may be designed to prevent the introduction of air bubbles into the indicator pathway. Also, a check valve 325 may be used to prevent backflow of fluid from the indicator pathway back into the milk cavity. The check valve 325 may be placed anywhere within or on either end of the indicator pathway. Multiple check valves may also be used. Although the check valve may be placed anywhere within or on either end of the indicator pathway, one exemplary placement includes, but is not limited to, the placement of the check valve 325 at the end of the indicator pathway as shown in FIGS. 3-6.

While IFMD is illustrated with respect to attachment to a mother's breast, those skilled in the art will appreciate that the IFMD may be utilized as a nipple on a bottle for bottle-fed babies. Similarly, the FMD may be utilized with a bottle-fed baby.

Figure 5:
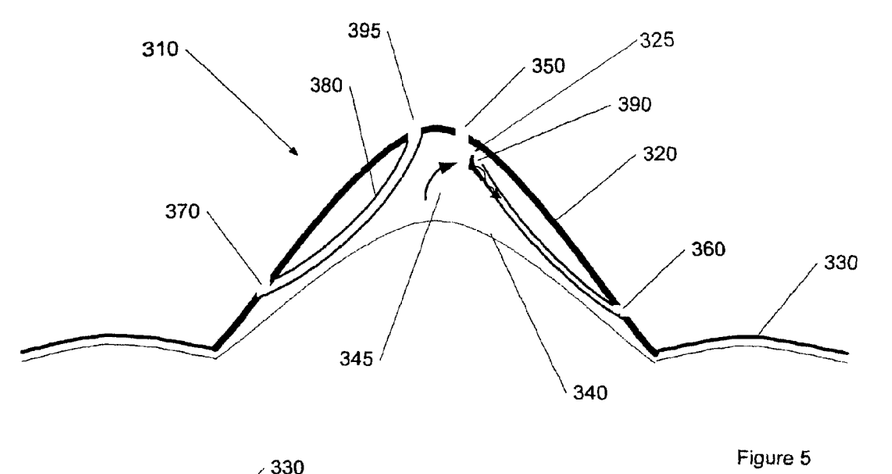
FIG. 5 illustrates the flow of breast milk from the milk cavity area into the indicator pathway in a cross-sectional side view of an IFMD consistent with the present invention.
Figure 6:
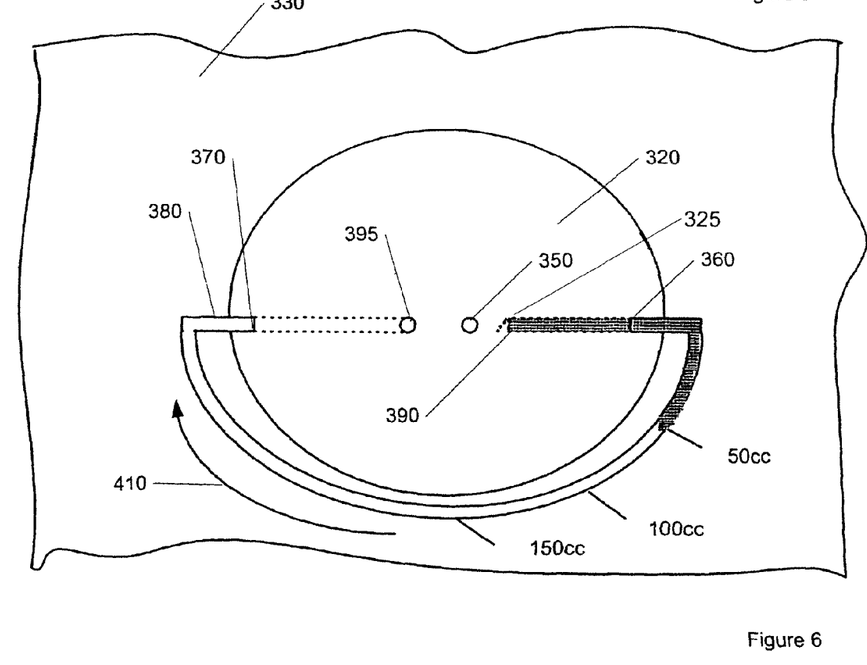
FIG. 6 illustrates the flow of breast milk from the milk cavity area 345 into the indicator pathway in a top view of an IFMD consistent with the present invention.

FIG. 5 illustrates the flow of breast milk from the milk cavity area 345 into the indicator pathway 380 in a cross-sectional side view of an IFMD consistent with the principles of the present invention. FIG. 6 illustrates the flow of breast milk from the milk cavity area 345 into the indicator pathway 380 in a top view of an IFMD consistent with the principles of the present invention. As indicated by the shaded region of the indicator pathway 380, milk flows from the milk cavity area 345 into aperture 390 of the indicator pathway 380 as the baby sucks on aperture 395 of the indicator pathway 380.

As previously mentioned, the path taken by the indicator pathway may vary in different embodiments consistent with the present invention.

Figure 7:
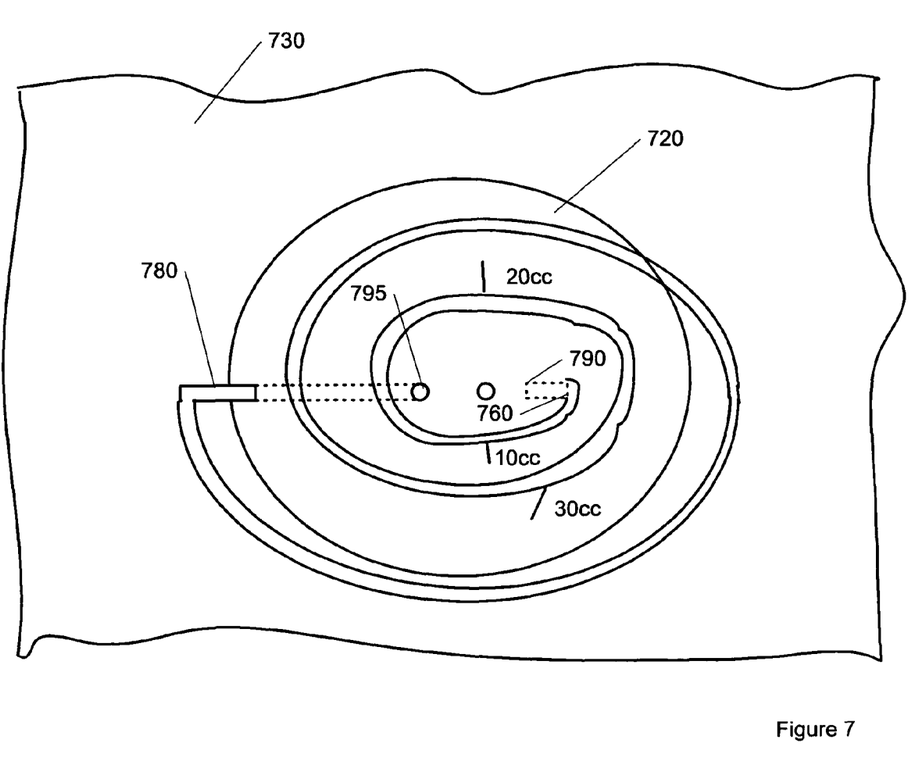
FIG. 7 illustrates a top-down view of an IFMD with a helical indicator pathway consistent with the present invention.

FIG. 7 illustrates a top-down view of an IFMD with a helical indicator pathway consistent with the present invention. In this illustration, a helical indicator pathway 780 begins at sucking aperture 795 and helically coils around the nipple base 730 or nipple tip 720, through a transition aperture 760 into the milk cavity, and ending in milk cavity aperture 790. This indicator pathway 780 provides for an extended, and more detailed, use of gradations for finer indication of fluid consumption.

Various combinations of apertures and connections may be utilized consistent with the present invention. Example of which are illustrated below in FIGS. 8 and 9.

Figure 8:
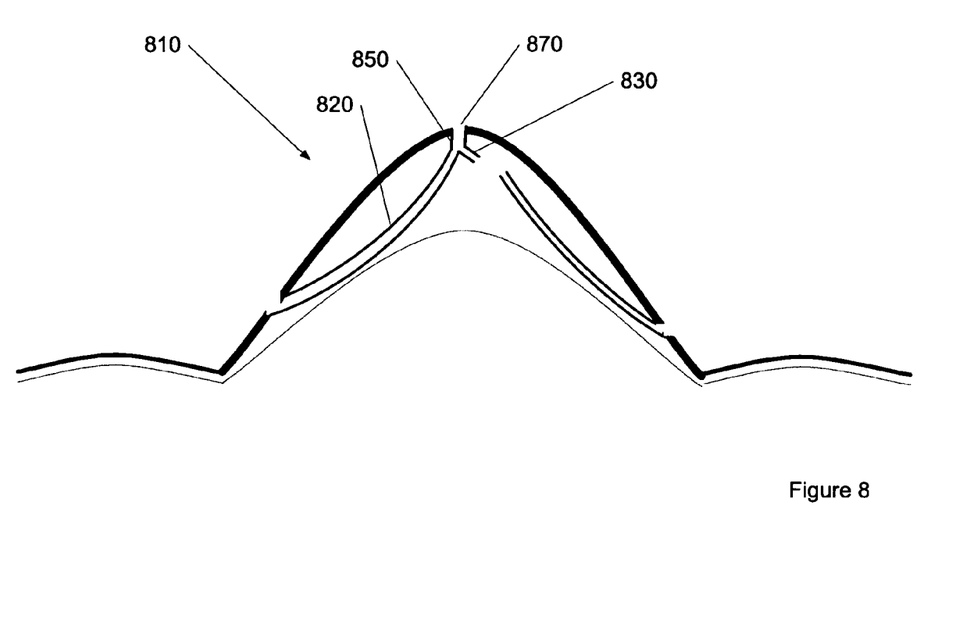
FIG. 8 illustrates an IFMD with a Y-shaped pressure delivery pathway for providing suction from the baby's mouth to the feeding pathway and the indicator pathway consistent with the present invention.

For example, FIG. 8 illustrates an IFMD 810 with a Y-shaped pressure delivery pathway for providing suction from the baby's mouth to the feeding pathway and the indicator pathway consistent with the present invention. The IFMD 810 is similar in structure to IFMD 310, but includes a pressure delivery pathway 850. The pressure delivery pathway 850 may be an inverted Y-shaped connecter with an aperture 870 to the baby's mouth for communicating pressure through the Y-branches to the indicator pathway 820 and the feeding pathway 830. The pressure delivery pathway helps to ensure that equal pressure is applied to both the indicator pathway 820 and the feeding pathway 830.

Figure 9:
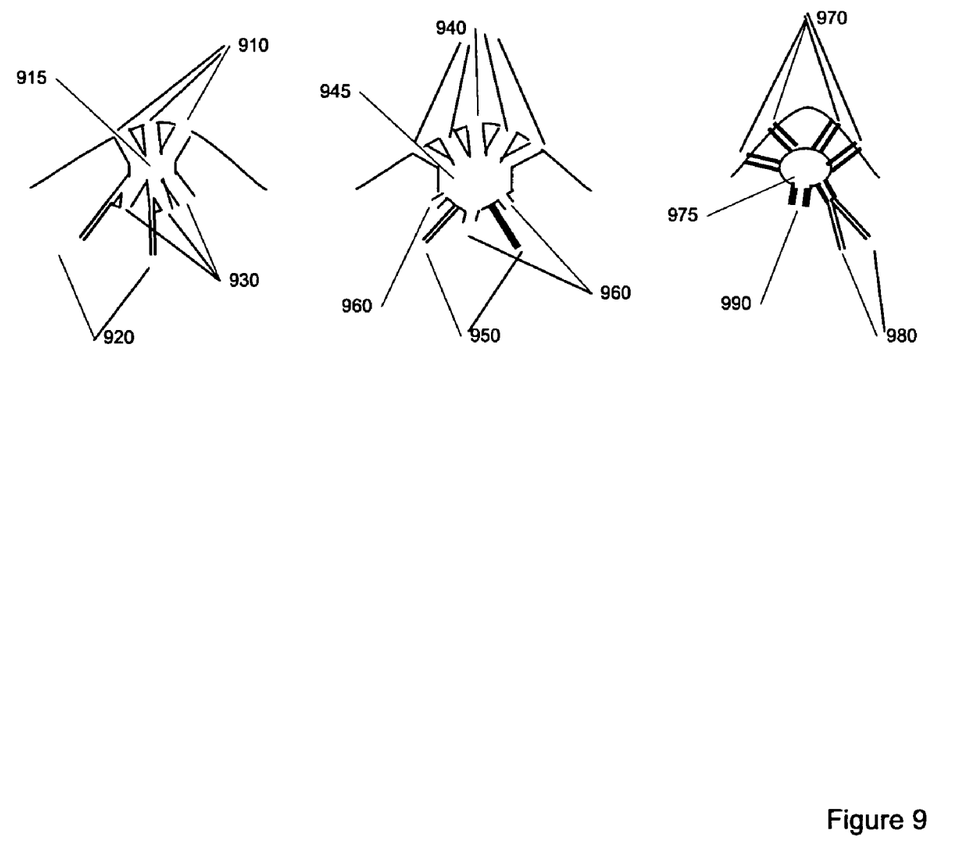
FIG. 9 illustrates a variety of apertures, pressure delivery pathways, feeding pathways, and indicating pathways that may be utilized consistent with the present invention.

FIG. 9 illustrates a variety of apertures, pressure delivery pathways, feeding pathways, and indicator pathways that may be utilized consistent with the present invention. Three configurations are illustrated. In the leftmost configuration, three apertures 910 provide pressure from a baby's mouth to the pressure delivery pathway 915. Two indicator pathways 920 are in communication with the pressure delivery pathway 915. Also, three feeding pathways 930 are in communication with the pressure delivery pathway 915.

In the middle configuration, five apertures 940 are in communication between the baby's mouth and the pressure delivery pathway 945. Two indicator pathways 950 are in communication with the pressure delivery pathway 945. And, three feeding pathways 960 are in communication with the pressure delivery pathway 945.

In the rightmost configuration, four apertures 970 are in communication between the baby's mouth and the pressure delivery pathway 975. Two indicator pathways 980 are coupled and in communication with the pressure delivery pathway 975. And, a single feeding pathway 990 is in communication with the pressure delivery pathway 975.

Figure 10:
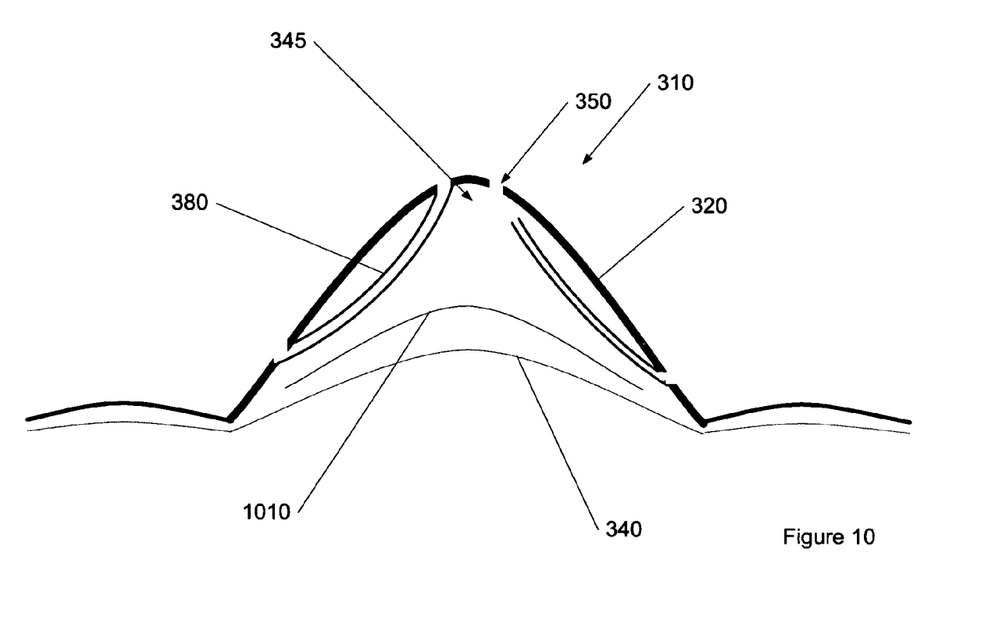
FIG. 10 illustrates the IFMD with the use of a comfort pad consistent with the present invention.

FIG. 10 illustrates the IFMD 310 with the use of a comfort pad 1010 consistent with the present invention. A comfort pad 1010 may be placed between the woman's breast 340 and the nipple tip 320, so as to provide a degree of comfort and protection between the breast 340 and the nipple tip 320. The comfort pad 1010 may be designed to allow the passage of breast milk through the comfort pad 1010. The comfort pad 1010 may protect the nipple 340 from touching the indicator pathway 380 and feeding pathway 350. The comfort pads may be detached from the IFMD 310 or attached to the IFMD 310.

Figure 11:
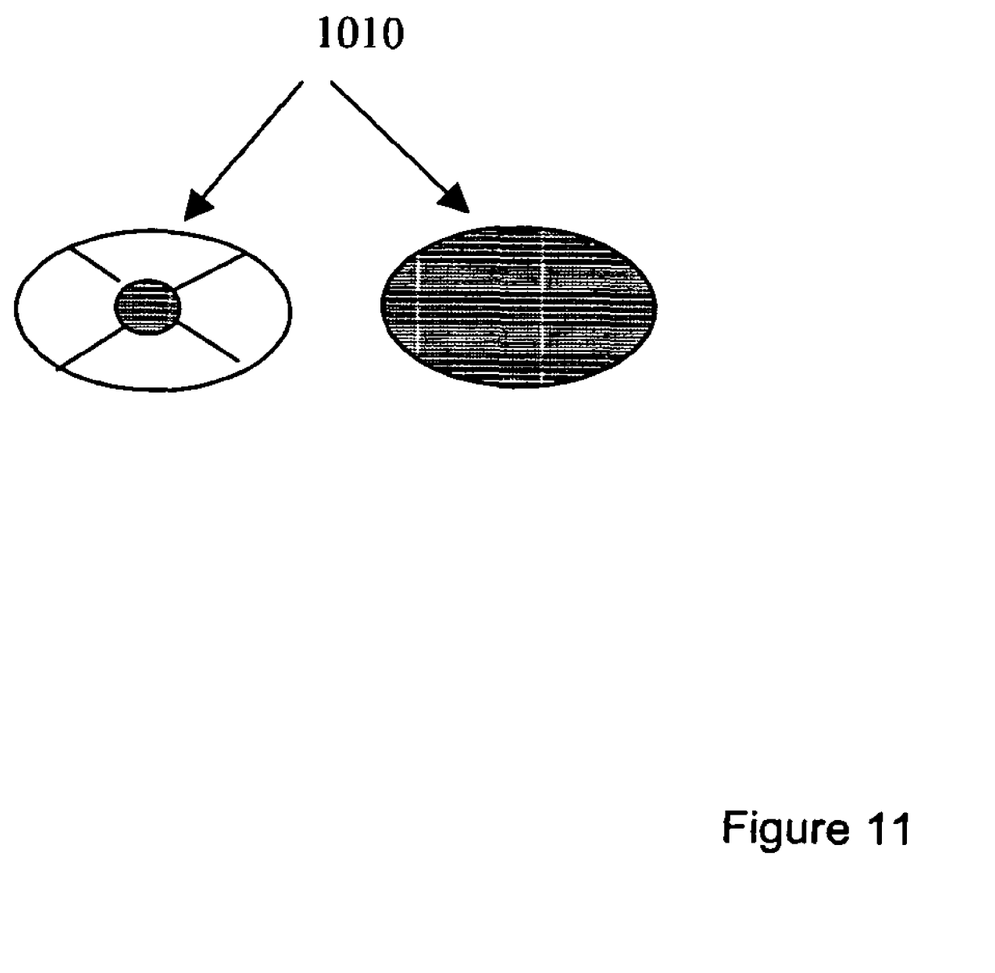
FIG. 11 illustrates a top view of two embodiments of the comfort pad consistent with the present invention.

FIG. 11 illustrates a top view of two embodiments of the comfort pad 1010 consistent with the present invention. Two typical embodiments of comfort pad 1010 are shown in FIG. 11. The comfort pads may be constructed of any number of materials known to those skilled in the art, including, for example, gauze.

Figure 12:
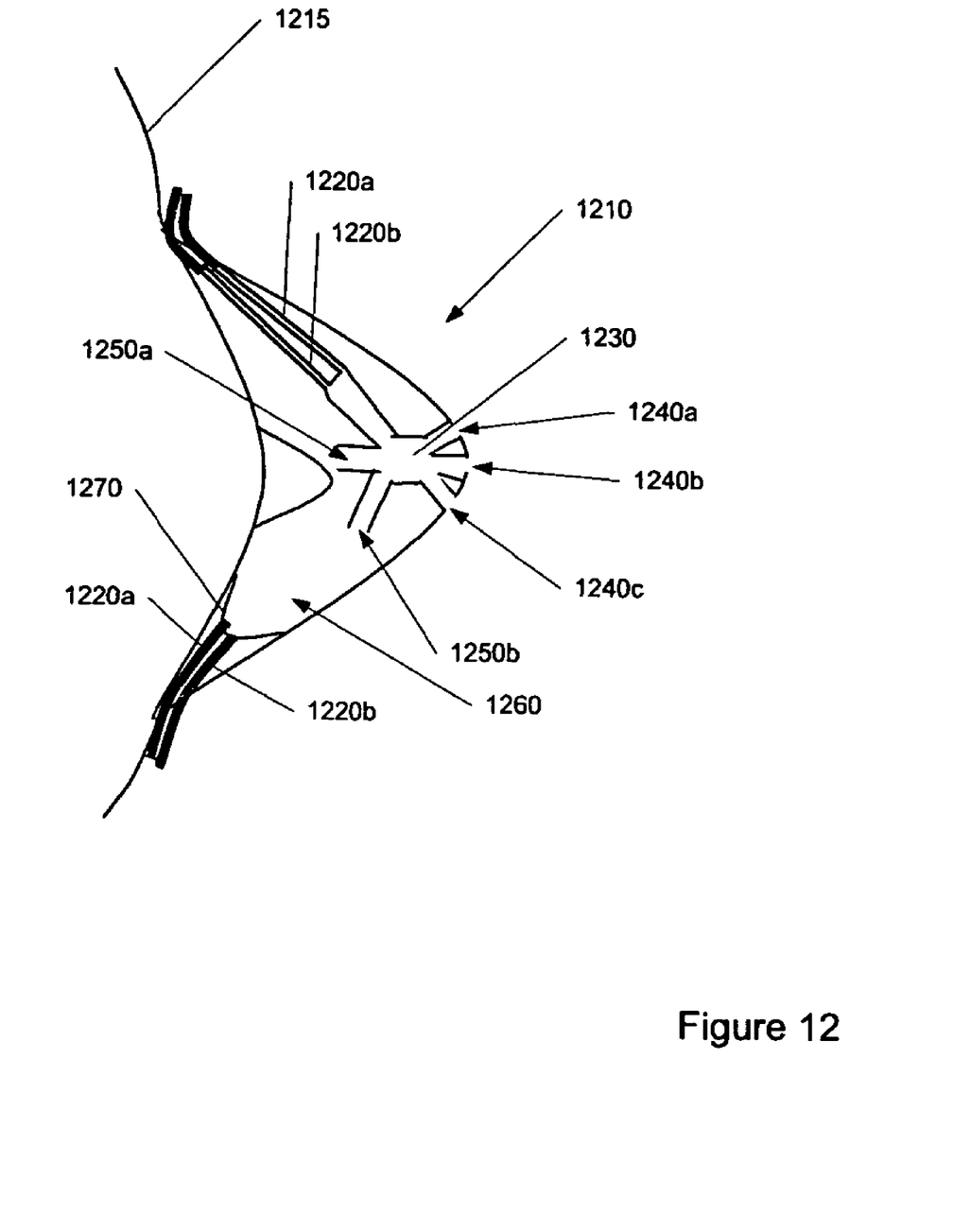
FIG. 12 illustrates a milk collection reservoir utilized with an IFMD consistent with the present invention.

FIG. 12 illustrates a milk collection reservoir 1270 utilized with an IFMD 1210 consistent with the present invention. As illustrated, IFMD 120 is affixed to the mother's breast 1215 and comprises two indicator pathways 1220*a,b*. A baby provides suction through apertures 1240*a,b,c* to a pressure delivery pathway 1230. Pressure delivery pathway 1230 provides the baby's pressure to two feeding pathways 1250*a,b* that draw milk from the milk cavity area 1260. The pressure applied from the baby's sucking is applied to both indicator pathways 1220*a,b* and the two feeding pathways 1250*a,b*. The milk collection reservoir 1270, in this example a cup like device, may be juxtaposed between the nipple tip of the IFMD 1210 and the breast 1215 and located at the bottom of the IFMD 1210. The milk collection reservoir 1270 retains milk from the milk cavity area 1260 for providing to the intakes of the indicator pathways 1220*a,b*. Milk collection reservoir 1270 acts to serve as a consistent store of milk to prevent air bubbles from entering the indicator pathways 1220*a,b*. While milk collection reservoir 1270 is illustrated in conjunction with an IFMD having multiple feeding pathways and indicator pathways, it should be appreciated that milk collection reservoir 1270 may be utilized in any of the configurations described herein.

Figure 13:
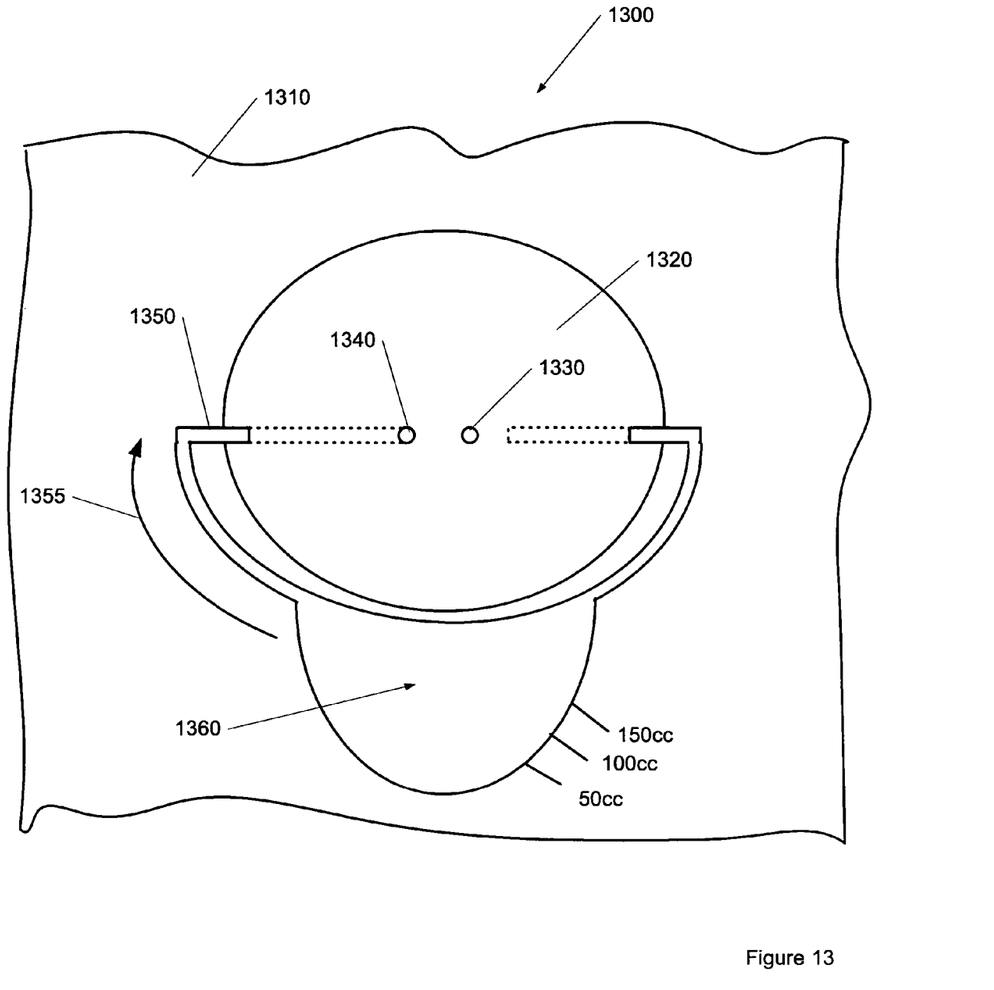
FIG. 13 illustrates a milk indicator reservoir utilized with an IFMD consistent with the present invention.

FIG. 13 illustrates a milk indicator reservoir 1360 utilized with an IFMD 1310 consistent with the present invention. As illustrated, IFMD 1310 is affixed to the mother's breast and comprises an indicator pathway 1350. A baby provides suction in the nipple 1320 through aperture 1340 to indicator pathway 1340 and provides suction to feeding pathway 1330. The milk indicator reservoir 1310 may be placed in the indicator pathway 1350. As milk is drawn from the mother's breast through indicator pathway 1350, the milk accumulates in milk indicator reservoir 1360. The milk indicator reservoir 1360 may be marked to indicate the quantity of milk drawn through the feeding pathway 1330. The milk indicator reservoir 1360 may be designed of such a volume to be able to indicate an amount of milk greater than or equal to a typical feeding session's intake. While not required to practice the principles of the present invention, use of the milk indicator reservoir 1360 assists in preventing possibly faulty readings that may result from air bubbles entering the indicator pathway 1350 in embodiments not having a milk indicator reservoir 1360 or a milk collection reservoir. While milk indicator reservoir 1360 is illustrated in conjunction with an IFMD having a single feeding pathway and a single indicator pathway, it should be appreciated that milk indicator reservoir 1360 may be utilized in any of the configurations described herein.

Figure 14:
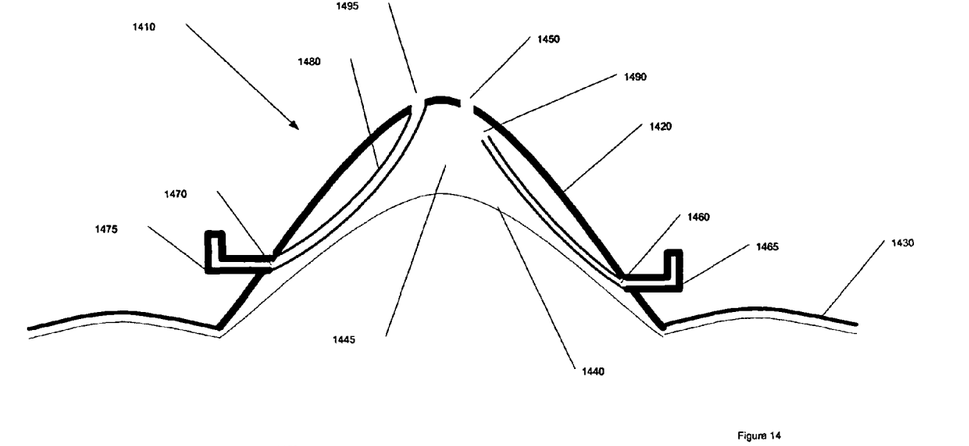
FIG. 14 illustrates a cross-sectional side view of an IFMD having a detachable indicator pathway (shown in FIG. 15) consistent with the present invention.

FIG. 14 illustrates a cross-sectional side view of an IFMD 1410 having a detachable indicator pathway 1510 (shown in FIG. 15) consistent with the present invention. The IFMD 1410 is affixed to a woman's breast 1440. The nipple tip 1420 merges into a nipple base 1430. When placed upon the breast 1440, a milk cavity area 1445 is formed between the nipple tip 1420 and the breast 1440. When a baby sucks on the nipple tip 1420, negative pressure is transmitted through the feeding pathway 1450 that communicates the pressure from the baby's mouth to the breast 1440. This draws milk into the milk cavity area 1445 and into the baby's mouth through the feeding pathway 1450. While a single feeding pathway 1450 is illustrated in FIG. 14, those skilled in the art will appreciate that multiple feeding pathways 1450 of various shapes, sizes, and arrangements could be used.

As the baby applies negative pressure through feeding pathway 1450, the same negative pressure is applied to a first portion of indicator pathway 1480 at first aperture 1495. A final portion of indicator pathway 1480 has a second aperture 1490 in communication with the milk cavity area 1445, so that the pressure is transmitted through the indicator pathway 1480 to draw milk from the milk cavity area 1445 into the indicator pathway 1480 through second aperture 1490. In this illustrated embodiment, the indicator pathway 1480 comprises the first portion of the indicator pathway that ends at first portion attachment 1475 and the second portion of the indicator pathway that ends at a second portion attachment 1465. Between the first portion attachment 1475 and the second portion attachment 1465, a detachable indicator pathway 1510 (shown below in FIG. 15) may be placed. The detachable indicator pathway 1510 provides fluid communication between the first portion of the indicator pathway and the second portion of the indicator pathway. Indicator pathway 1480 is more readily seen and understood with respect to FIG. 15.

Figure 15:
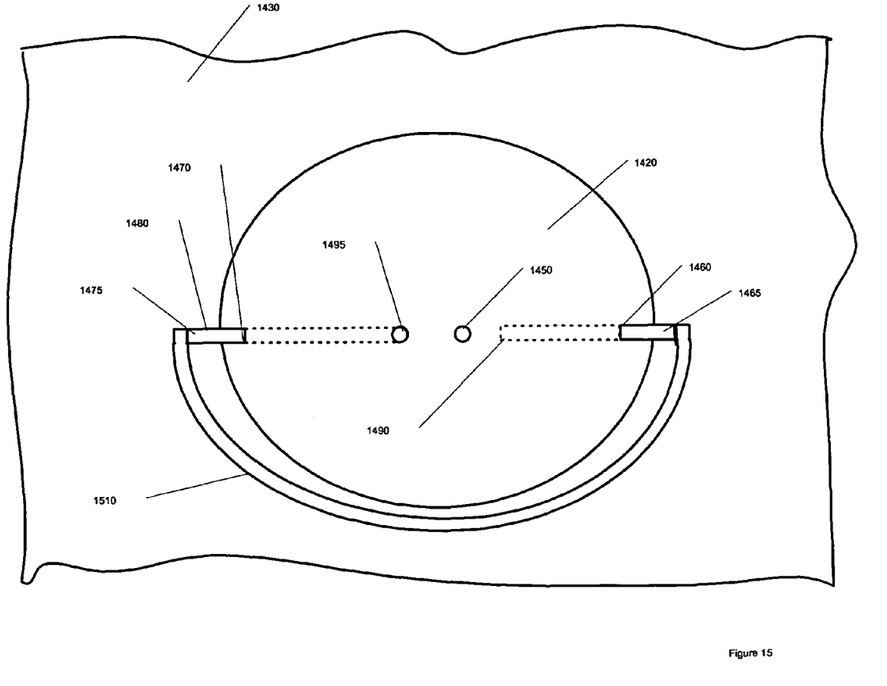
FIG. 15 illustrates a top-down view of the IFMD of FIG. 14 consistent with the present invention.

FIG. 15 illustrates a top-down view of the IFMD of FIG. 14 consistent with the present invention. In the illustrated IFMD, the indicator pathway second aperture 1490 opens into the milk cavity area 1445. The indicator pathway 1480 then exits through a first nipple tip transition aperture 1460 to the second portion attachment 1465. Attached to the second portion attachment 1465, the detachable indicator pathway 1510 traverses to the first portion attachment 1475 which communicates through a second nipple tip transition aperture 1470 to the first aperture 1495 to receive the baby's sucking negative pressure. As the baby sucks, the indicator pathway intakes milk.

Gradations may be placed at one or more points along the detachable indicator pathway 1510, so that the total volume of fluid received by the baby through the feeding pathway can be read. Those skilled in the art will appreciate that gradations are not necessary to indicate fluid flow, but are merely useful in indicating approximate amounts of fluid taken by the baby. For example, it is consistent with the principles of the present invention to provide no gradations or to provide a single gradation to indicate when the baby has taken in a sufficient amount. Or, for example, a colored zone may be used to indicate an appropriate intake for the baby.

The indicator pathway may have markings or gradiations at one or more points along its length, indicating the total volume of fluid flow through the feeding pathway. Since the indicator pathway may be made from a transparent material, the white milk or formula front advancing along the indicator pathway may provide a visual indicator, similar to a common mercury thermometer.

Given the physical characteristics of the indicator and feeding pathways, for example, the length, diameter, resistance, and number of pathways, the amount of fluid, milk or formula, at each point during the feeding process can be approximately calculated.

The following calculations are given for feeding and indicator pathways that are round. Those skilled in the art will appreciate that these calculations can be modified to account for feeding and indicator pathways of various shapes.

For example, for a given FMD with a single indicator pathway, the resistance of the indicator pathway, $R_{IP}$, may be calculated as a function of the length and diameter of the indicator pathway:

$$R_{IP} = \frac{L_{IP}}{D_{IP}} \quad (1)$$

where $L_{IP}$ is the length of indicator pathway and $D_{IP}$ is the diameter of indicator pathway Similarly, the resistance of the feeding pathway, $R_{FP}$, can be calculated as a function of the length and diameter of the feeding pathway:

$$R_{FP} = \frac{L_{FP}}{D_{FP}} \quad (2)$$

where $L_{FP}$ is the length of the feeding pathway;
and $D_{FP}$ is the diameter of the feeding pathway Those skilled in the art will appreciate that the resistance of the indicator pathway may also be impacted by the portion of the indicator pathway that is filled with fluid, increasing the resistance of the indicator pathway. For more exacting measurement, the gradiations may be placed on the indicator pathway to compensate for this non-linearity. The viscosity of the fluid may also impact the resistance. Therefore, the calculations described are approximate. In practice, calibrations may be performed in order to provide more precise gradation calculations.

For unbiased split pathways, where the pressure drop induced by the baby's sucking is the same on the feeding pathway and the indicator pathway, an FMD ratio (the resistances ratio of the indicator pathway and the feeding pathway), $S_{FMD}$, can then be calculated as:

$$S_{FMD} = C * \frac{R_{IP}}{R_{FP}} = C * \frac{L_{IP} * D_{FP}}{L_{FP} * D_{IP}} \quad (3)$$

where C is a calibration coefficient to account for different calibration parameters.

The FMD ratio, $S_{FMD}$, actually represents the ratio between the amount of fluid in the indicator pathway(s) related to the total amount of fluid that dispensed through the feeding pathway.

The amount of fluid in the indicator pathway can easily be calculated given the length of the indicator pathway filled with fluid and the cross-sectional area, for example, the radius in a round indicator pathway, of the indicator pathway.

$$V_{IP}=(CS)L$$

$$V_{IP}=\pi r^2 L \quad (4)$$

where $V_{IP}$ is the volume of the filled portion of the indicator pathway; r is the radius of the indicator pathway; L is the length of the filled portion of the indicator pathway; and CS is the cross-sectional area of the indicator pathway.

Therefore, throughout the feeding process, the amount of fluid received by the baby (or flow out of the feeding pathways) is:

$$V_{FP}=V_{IP}*S_{FMD} \quad (5)$$

where $V_{FP}$ is the volume of fluid through the feeding pathway.

While the above calculations are illustrated for calculating resistance with single feeding and indicator pathways, the calculations for two feeding pathways and a single indicator pathway are presented below. The resistance for the combined feeding pathways is calculated as follow, $R_{FP1}$ is the resistance for the first feeding pathway and $R_{FP2}$ is the resistance for the second feeding pathway:

$$R_{(FP1+FP2)} = \frac{R_{FP1}*R_{FP2}}{R_{FP1}+R_{FP2}}$$

therefore the resistance ratio, $S_{FMD}$, for single indicator pathway and two feeding pathways is:

$$S_{FMD} = C * \frac{R_{IP}}{R_{(FP1+FP2)}} = C * \left(\frac{R_{IP}*(R_{FP1}+R_{FP2})}{R_{FP1}*R_{FP2}}\right) \quad (6)$$

where C is a calibration coefficient to account for different calibration parameters. Those skilled in the art will appreciate that other ratios may be calculated for other combinations of feeding and indicator pathways.

The table below illustrates results from a typical implementation of the above calculations, with the first portion indicating results for implementations having a single indicator pathway and a single feeding pathway and the second portion indicating results for a single indicator pathway and dual feeding pathways:

| Single Indicator Pathway (IP) and Single Feeding Pathway (FP) | |
|---|---|
| IP Diameter | 0.1 |
| IP Length | 15.0 |
| $R_{IP}$ | 150 |
| FP Diameter | 0.2 |
| FP Length | 0.075 |
| $R_{FP}$ | 0.375 |
| $S_{FMD}$ Coefficient | 1 |
| $S_{FMD}$ | 400 |
| Volume of Full IP | 0.11775 |
| Amount of Milk Dispensed through FP | 47.1 |
| Single Indicator Pathway (IP) and Double Feeding Pathways (FP1 and FP2) | |
| IP Diameter | 0.1 |
| IP Length | 12.0 |
| $R_{IP}$ | 120 |
| FP1 Diameter | 0.2 |
| FP1 Length | 0.075 |
| $R_{FP1}$ | 0.375 |
| FP2 Diameter | 0.2 |
| FP2 Length | 0.075 |
| $R_{FP2}$ | 0.375 |
| $S_{fmd}$ Coefficient | 1 |
| Combined resistance of both FPs | 0.1875 |
| $S_{FMD}$ | 640 |
| Volume of Full IP | 0.0942 |
| Amount of Milk Dispensed through both FP1 and FP2 | 60.288 |

The foregoing description of possible implementations consistent with the present invention does not represent a comprehensive list of all such implementations or all variations of the implementations described. The description of only some implementations should not be construed as intent to exclude other implementations. Those skilled in the art will understand how to implement the invention in the appended claims in many other ways, using equivalents and alternatives that do not depart from the scope of the following claims. Moreover, unless indicated to the contrary in the preceding description, none of the components described in the implementations is essential to the invention. In addition, to the extent the conjunctive "and" is used it shall be deemed to mean either "and" or "or." Also, "or" shall be deemed to mean either the exclusive disjunctive or inclusive disjunctive form.

The invention claimed is:
1. A method of measuring fluid flow from a fluid source to a baby's mouth through a nipple comprising:
providing at least one feeding pathway for fluid flow from the fluid source to the baby's mouth, wherein the feeding pathway has a first opening adapted to be in communi- cation with the fluid source and a second opening adapted to be in direct communication with the baby's mouth; and providing at least one indicator pathway having a different length from the feeding pathway for indicating an amount of fluid provided to the baby's mouth through the feeding pathway, wherein the indicator pathway has a first opening adapted to be in communication with the fluid source and a second opening adapted to be in direct fluid communication with the baby's mouth, receiving suction from the baby's mouth;

providing the suction to the feeding pathway and the indicator pathway; and measuring the amount of fluid drawn into and retained in the indicator pathway, whereby the amount of fluid drawn into and retained in the indicator pathway is indicative of the amount of fluid drawn into the feeding pathway.

2. The method of claim 1, wherein the indicator pathway and the feeding pathway each have a cross-sectional area, and wherein the cross-sectional area of the indicator pathway is substantially smaller than the cross-sectional area of the feeding pathway.

3. The method of claim 1, wherein the indicator pathway and the feeding pathway each have a length, and wherein the length of the indicator pathway is substantially longer than the length of the feeding pathway.

4. The method of claim 1, further comprising: providing a pressure delivery pathway connecting the second opening of the feeding pathway and the second opening of the indicator pathway, and adapted to be connected to the baby's mouth.

5. The method of claim 1, further comprising providing a plurality of indicator pathways.

6. The method of claim 1, wherein the feeding pathway and the indicator pathway are integral to the nipple.

7. The method of claim 1, further comprising: providing gradations along the indicator pathway to indicate the amount of fluid provided to the baby's mouth through the feeding pathway.

8. The method of claim 1, further comprising: providing a plurality of feeding pathways to provide fluid from the fluid source to the baby's mouth.

9. The method of claim 1, wherein the fluid comprises breast milk, and wherein the feeding pathway and the indicator pathway are adapted to receive the breast milk from a mother's breast.

10. The method of claim 9, further comprising providing a comfort pad adapted to be disposed between the mother's breast and the indicator pathway.

11. The method of claim 9, further comprising providing a milk collection reservoir, wherein the milk collection reservoir is disposed between the fluid source and the first opening of the indicator pathway such that it is adapted to maintain a supply of breast milk to prevent air bubbles from entering the indicator pathway.

12. The method of claim 9, further comprising providing a milk indicator reservoir, wherein the milk indicator reservoir is positioned in the indicator pathway.

13. The method of claim 1, wherein the fluid source is a bottle.

14. The method of claim 1, further comprising: providing a check valve in the indicator pathway to prevent the backflow of fluid.

15. The method of claim 1, wherein the indicator pathway further comprises a detachable indicator pathway.

16. An apparatus, comprising:

at least one feeding pathway for fluid flow from a fluid source to a baby's mouth, wherein the feeding pathway has a first opening adapted to be in communication with the fluid source and a second opening adapted to be in direct communication with the baby's mouth; and at least one indicator pathway having a different length from the feeding pathway for indicating an amount of fluid provided to the baby's mouth through the feeding pathway, wherein the indicator pathway has a first opening adapted to be in communication with the fluid source and a second opening adapted to be in direct fluid communication with the baby's mouth, whereby the amount of fluid drawn into and retained in the indicator pathway is indicative of the amount of fluid drawn into the feeding pathway, configured such that the amount of fluid provided to the baby's mouth through the feeding pathway is proportional to the amount of fluid drawn into and retained in the indicator pathway.

17. The apparatus of claim 16, wherein the indicator pathway and the feeding pathway each have a cross-sectional area, and wherein the cross-sectional area of the indicator pathway is substantially smaller than the cross-sectional area of the feeding pathway.

18. The apparatus of claim 16, wherein the indicator pathway and the feeding pathway each have a length, and wherein the length of the indicator pathway is substantially longer than the length of the feeding pathway.

19. The apparatus of claim 16, further comprising: a pressure delivery pathway connecting the second opening of the feeding pathway and the second opening of the indicator pathway, and adapted to be connected to the baby's mouth.

20. The apparatus of claim 16, further comprising a plurality of indicator pathways.

21. The apparatus of claim 16, wherein the feeding pathway and the indicator pathway are integral to a nipple.

22. The apparatus of claim 16, further comprising: gradations along the indicator pathway to indicate the amount of fluid provided to the baby's mouth through the feeding pathway.

23. The apparatus of claim 16, further comprising: a plurality of feeding pathways to provide fluid from the fluid source to the baby's mouth.

24. The apparatus of claim 16, wherein the fluid comprises breast milk, and wherein the feeding pathway and the indicator pathway are adapted to receive the breast milk from a mother's breast.

25. The apparatus of claim 24, further comprising a comfort pad adapted to be disposed between the mother's breast and the indicator pathway.

26. The apparatus of claim 24, further comprising a milk collection reservoir, wherein the milk collection reservoir is disposed between the fluid source and the first opening of the indicator pathway such that it is adapted to maintain a supply of breast milk to prevent air bubbles from entering the indicator pathway.

27. The apparatus of claim 24, further comprising a milk indicator reservoir, wherein the milk indicator reservoir is positioned in the indicator pathway.

28. The apparatus of claim 16, wherein the fluid source is a bottle.

29. The apparatus of claim 16, further comprising: a check valve in the indicator pathway to prevent the backflow of fluid.

30. The apparatus of claim 16, wherein the indicator pathway further comprises a detachable indicator pathway.

* * * * *